United States Patent

Juhasz

Patent Number: 5,323,786
Date of Patent: Jun. 28, 1994

[54] DIGIT POSITIONING DEVICE FOR X-RAYS

[76] Inventor: Irene Juhasz, 110-20 73rd Rd., Forest Hills, N.Y. 11375

[21] Appl. No.: 889,456

[22] Filed: May 27, 1992

[51] Int. Cl.$^5$ ............................................. A61F 5/00
[52] U.S. Cl. ................................... 128/845; 128/880; 5/646
[58] Field of Search ............... 128/845, 846, 848, 878, 128/879, 880, 892, 858–862, 869, 891; 606/204.45; 433/140, 136, 137; 378/208; 5/623, 646, 647; 132/73, 285

[56] References Cited

U.S. PATENT DOCUMENTS

| | | | |
|---|---|---|---|
| 2,662,534 | 12/1953 | Swartz | 132/73 |
| 2,676,597 | 4/1954 | Colbert | 132/73 |
| 2,795,838 | 6/1957 | McNeely | 5/646 X |
| 3,434,470 | 3/1969 | Strickland | 128/848 |
| 3,705,585 | 12/1972 | Saffro | 433/136 X |
| 4,296,766 | 10/1981 | Benis | 132/73 |
| 4,321,890 | 3/1982 | Lange et al. | 128/845 X |
| 4,581,754 | 4/1986 | Donovan | 128/845 X |
| 4,782,825 | 11/1988 | Lonardo | 602/21 |
| 4,915,331 | 4/1990 | Becka et al. | 132/73 X |
| 5,020,547 | 6/1991 | Strock | 128/891 |
| 5,174,284 | 12/1992 | Jackson | 128/859 X |

*Primary Examiner*—Robert A. Hafer
*Assistant Examiner*—Brian E. Hanlon
*Attorney, Agent, or Firm*—Cohen, Pontani, Lieberman & Pavane

[57] ABSTRACT

The present invention is an X-ray transparent orthopedic device (10) for positioning a selected digit away from the adjacent digits facilitate the taking of X-rays. The device (10) comprises a first centrally located elongated longitudinal support (12) having a contoured upper surface (18) for the selected digit, and second and third elongated longitudinal supports (14) and (16), respectively, on either side of the support (12). Partitions (30, 32) and side walls (34, 36) depending from supports (14, 16) define channels (38, 40) for the adjacent digits.

9 Claims, 2 Drawing Sheets

DIGIT POSITIONING DEVICE FOR X-RAYS

BACKGROUND OF THE INVENTION

1. Field of the Invention

This invention pertains to orthopedic devices for positioning human digits for examination purpose. More particularly, the present invention pertains to orthopedic devices for positioning an injured digit to facilitate the taking of X-rays.

2. Prior Art

A wide variety of orthopedic devices for positioning various body parts are commercially available. Most of these devices are used for positioning a body part after examination reveals an injury, such as a bone fracture, etc. When a bone is injured, a standard medical practice is to obtain X-rays of the injured area to determine if the bone is fractured. So, if a digit, such as a finger, is injured, the standard medical practice is to X-ray the finger.

When taking X-rays, it is highly desirable or obtain unobstructed multiple views of the injured area. To obtain unobstructed X-ray views of an injured finger, the injured finger must be spaced from the other fingers and held relatively motionless. Traditionally, this is accomplished by anchoring the injured finger and the adjacent fingers with, for example, first aid tape. While this approach is effective in positioning the injured finger away from the adjacent fingers, if often causes discomfort to the patient.

Therefore, it is an object of the invention to provide a device for positioning an injured finger in spaced relation from the adjacent fingers to obtain unobstructed X-ray views of the injured finger without causing unnecessary discomfort to the patient.

It is a further object of the invention to provide an orthopedic device capable of securing and displacing an injured digit vertically and horizontally relative to the adjacent digits to facilitate the taking of X-rays.

SUMMARY OF THE INVENTION

Broadly speaking, the present invention is an X-ray transparent orthopedic device for positioning a selected digit away from the digits on either side of the selected digit to facilitate the taking of X-rays comprising: a first elongated longitudinal support having a lower surface portion and an upper surface portion for supporting, on the upper surface portion, the underside of the selected digit; second and third elongated longitudinal supports joined to the first longitudinal support on either side thereof, the second and third longitudinal supports each having a lower surface portion for supporting the upper sides of the digits on either side of the selected digit, whereby the first, second and third elongated longitudinal supports retain the selected digit in a horizontal plane displaced from the digits on either side of the selected digit; a first partition depending substantially from the junction between the first and second longitudinal supports and a second partition depending substantially from the junction between the first and third longitudinal supports, the partitions retaining the digits on either side of the selected digit in vertical planes displaced from the selected digit; whereby the selected digit is vertically and horizontally displaced from the adjacent digits to facilitate the taking of X-rays.

In the preferred embodiment, the first longitudinal support is vertically displaced from the second and third longitudinal supports and the device further comprises a pair of side walls depending from the free sides of the second and third longitudinal supports in substantially parallel relation with the first and second partitions for defining a pair of channels on either side of the first longitudinal support for receiving the digits adjacent the selected digit.

Also in the preferred embodiment, the first longitudinal support is inclined and its upper surface portion is contoured to facilitate the positioning of the selected digit.

The foregoing as well as additional details of the present invention will be more fully apparent from the following detailed description and annexed drawings of the presently preferred embodiments thereof.

DETAILED DESCRIPTION OF THE PREFERRED EMBODIMENT

Figure 1:
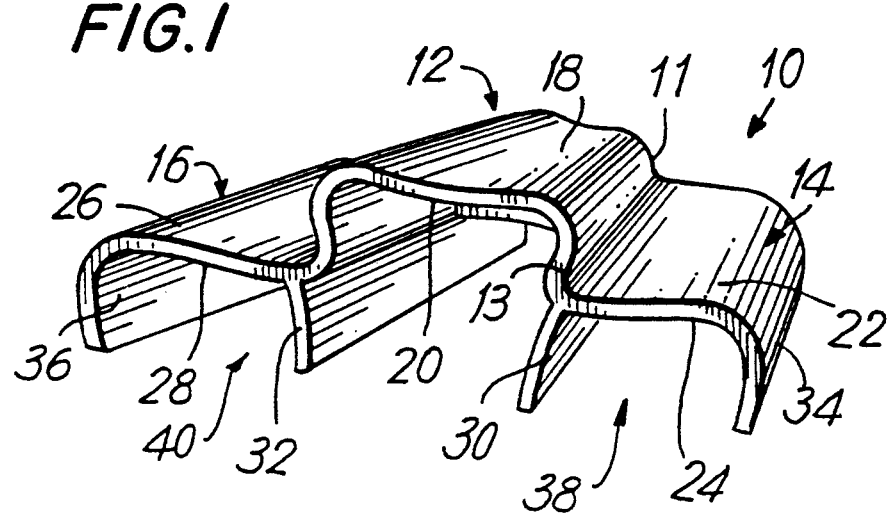
FIG. 1 is a perspective view of an orthopedic device in accordance with the present invention.
Figure 2:
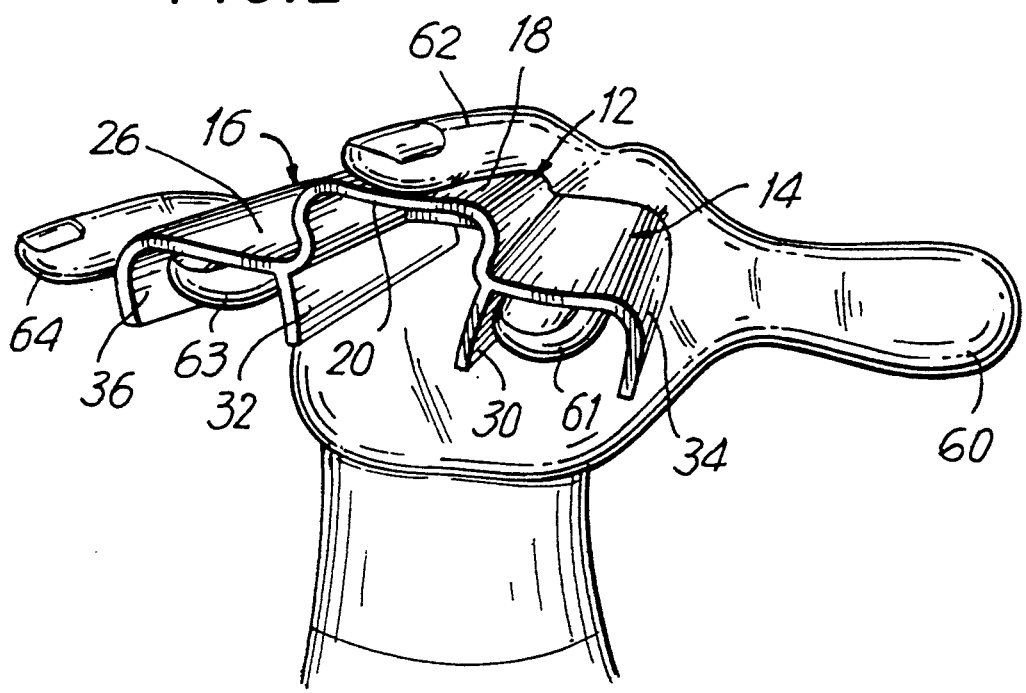
FIG. 2 is a perspective view of the orthopedic device in use.
Figure 3:
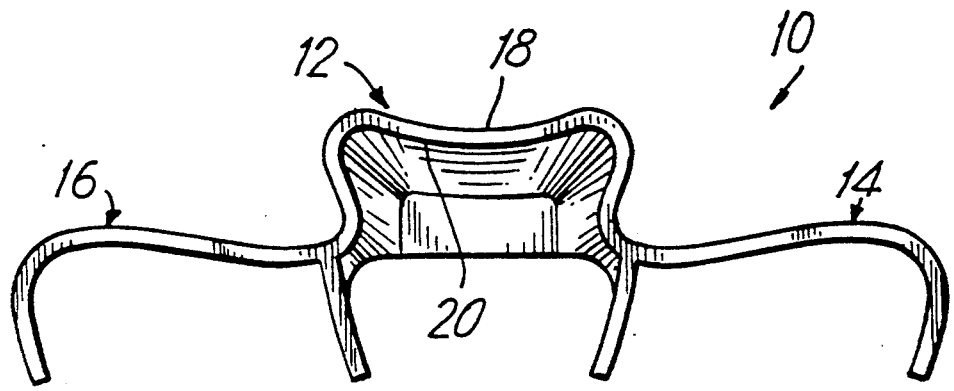
FIG. 3 is a front view of the device.

Referring now to the drawings, the device in accordance with the present invention is generally designated at 10. The device 10 has a front 11, a back 13, a first centrally located longitudinal support 12, and second and third longitudinal supports 14 and 16 positioned on either side of the first longitudinal support. The first longitudinal support 12 has an upper surface 18 and a lower surface 20. Likewise, second longitudinal support 14 has upper surface 22 and lower surface 24 and third longitudinal support 16 has upper surface 26 and lower surface 28. As best seen in FIGS. 1 and 2 and for reasons that will be apparent below, the first longitudinal support 12 is vertically offset from the second and third longitudinal supports 14, 16 and the upper surface portion 18 of support 12 is provided with a longitudinally extending central recess. As shown, the device also comprises a first partition 30 depending substantially from the junction between the first and second longitudinal supports, and a second partition 32 depending substantially from the junction between the first and third longitudinal supports. A pair of side walls 34, 36 depend from the free sides of the second and third longitudinal supports, respectively, thereby forming channels 38 and 40 in the bottom of the device 10 on either side of the first longitudinal support 12.

Figure 4:
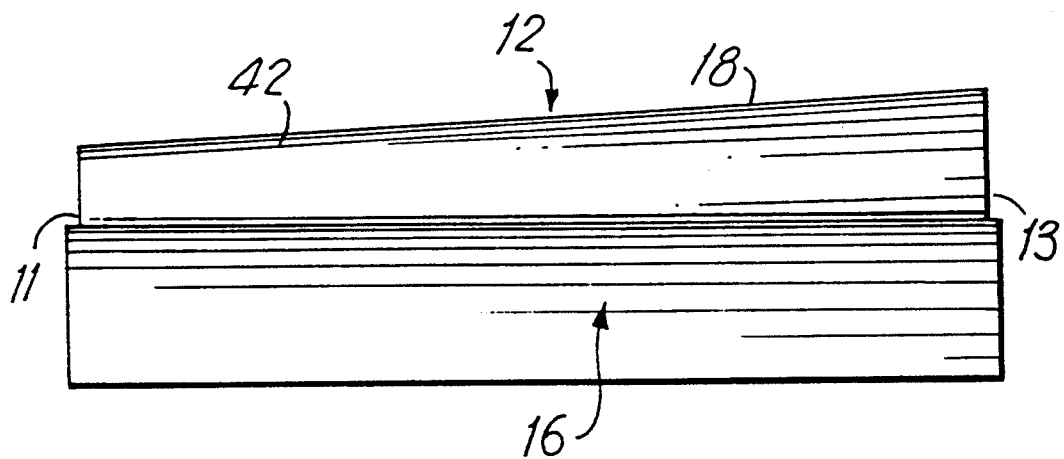
FIG. 4 is a side elevational view of the device as seen from the left in FIG. 1.

As shown in FIG. 4, the upper surface 18 of the first longitudinal support 12 is inclined, as shown at 42, from the front 11 to the back 13 of the device 10. As should by now be apparent and as shown in FIG. 2, when the device is in use, the incline 42 accommodates the physiology of the human hand by gradually raising selected finger 62 to a plane vertically displaced from fingers 61, 63 while the contoured upper surface portion 18 holds selected finger 62 relatively motionless. Simultaneously, the channels 38, 40 formed by partitions 30, 32, side walls 34, 36, and lower surfaces 24, 28, of second and third longitudinal supports 14, 16, respectively, serve to retain fingers 61, 63 vertically and horizontally displaced from finger 62. As explained above, and as shown in FIG. 2, once the device 10 is in place, the selected finger 62 is vertically and horizontally spaced from the adjacent fingers 61, 63 thus allowing a plurality of X-ray views of finger 62, including profiles, without the use of additional securing means and without obstruction by fingers 61, 63.

To obtain a clear image of the finger 62 with device 10 in place, the user's hand must remain motionless while X-rays are being taken. Generally, the user will simply hold his hand still. However, if for example, the user is a child, the device 10 may be taped down or otherwise secured to the examination table to ensure that the child's hand remains motionless during the X-ray procedure.

Although FIG. 2 shows finger 62 placed on first longitudinal support 12, the device 10 may be used to examine other injured fingers as well. For example, if finger 63 is to be X-rayed, this finger would be positioned on first longitudinal support 12 and fingers 64 and 62 would occupy channels 40 and 38, respectively. Similarly, the device 10 may be used to X-ray finger 64 by positioning finger 64 on the first longitudinal support 12 and finger 63 in channel 38. Since, in this application, no finger would occupy channel 40, adhesive tape may be used to secure the device 10 to the user's hand or to an examination table to provide stability.

In the preferred embodiment, the device may be manufactured by injection molding techniques utilizing any one of a variety of moldable thermoplastic resins, such as polystyrene. If incline 42 is removed, the device may also be manufactured by extrusion methods. Also, suitable downsized versions of the device 10 may be used for examining children's fingers and injured toes.

Although I have herein shown and described the preferred embodiment of the invention, various changes and modifications will be readily apparent to those of ordinary skill in the art who read the foregoing description. For example, channels 38 and 40 may be provided with bottom walls to better contain fingers 61 and 63. As this as well as further changes and modifications are intended to be within the scope of the present invention, the foregoing description should be construed as illustrative, and not in a limiting sense, the scope of the invention being defined by the following claims.

I claim:

1. An X-ray transparent orthopedic device for interposition between the digits of a human hand or foot for positioning a selected digit away from the digits on either side of said selected digit to facilitate the taking of an X-ray image comprising:

a first elongated longitudinal support having a lower surface portion and an upper surface portion for supporting, on said upper surface portion, the underside of said selected digit;

second and third elongated longitudinal supports each having a first side joined to said first elongated longitudinal support on either side of said first elongated, said second and third elongated longitudinal supports each having a lower surface portion for downwardly deflecting the upper sides of the digits on either side of said selected digit, whereby said first, second and third elongated longitudinal supports are capable of retaining said selected digit in a horizontal plane displaced from said digits on either side of said selected digit;

a first partition depending downwardly from the lower surface portion of the second longitudinal support substantially at the junction between said first and second elongated longitudinal supports, and a second partition depending downwardly from the lower surface portion of the third longitudinal support substantially at the junction between said first and third elongated longitudinal supports, said partitions are capable of retaining said digits on either side of said selected digit in vertical planes displaced from said selected digit;

said device being made of an X-ray transparent material so that said selected digit is vertically and horizontally displaced from said remaining digits to facilitate the taking of an X-ray image of said selected digit.

2. The orthopedic device of claim 1, wherein said first elongated longitudinal support is vertically displaced from said second and third elongated longitudinal supports.

3. The orthopedic device of claim 1 wherein said second elongated support has a second side with a first side wall depending therefrom, and wherein said third elongated longitudinal support has a second side with a first side wall depending therefrom, said side walls being in substantially parallel relation with said first and second partitions, for defining a pair of channels on either side of said first elongated longitudinal support for receiving the digits adjacent said selected digit.

4. The orthopedic device of claim 1, wherein said upper surface portion of said first elongated longitudinal support is inclined from one end of said device to the other.

5. The orthopedic device of claim 1, wherein said upper surface portion of said first longitudinal support is contoured to receive said selected digit.

6. The orthopedic device of claim 1, wherein said device is integrally formed.

7. The orthopedic device of claim 1, wherein said device comprises an extruded element.

8. A method for displacing a selected digit of a human hand or foot from the adjacent digits to facilitate the taking of unobstructed X-ray images of said selected digit, comprising the steps of:

providing an X-ray transparent orthopedic device comprising:

(1) a first elongated longitudinal support having a lower surface portion and an upper surface portion;

(2) second and third elongated longitudinal supports joined to said first elongated longitudinal support on either side of said first elongated longitudinal support, said second and third elongated longitudinal supports each having a lower surface portion;

(3) a first partition depending downwardly from the lower surface portion of the second elongated longitudinal support substantially at the junction between said first and second elongated longitudinal supports, and a second partition depending downwardly from the lower surface portion of the third elongated longitudinal support substantially at the junction between said first and third elongated longitudinal supports;

positioning the underside of said selected digit on said upper surface portion of said first elongated longitudinal support;

positioning a first digit on one side of said selected digit below said second elongated longitudinal support adjacent the lower surface portion thereof and adjacent said first partition for retaining said first digit below said upper surface portion of said first elongated longitudinal support and in horizontal and vertical displacement from said selected digit;

positioning a second digit on the other side of said selected digit below said third elongated longitudinal support adjacent the lower surface portion thereof and adjacent said second partition for retaining said second digit below said upper surface portion of said first elongated longitudinal support and in horizontal and vertical displacement from said selected digit;

so that when said orthopedic device is in place, an X-ray image of said selected digit can be obtained unobscured by interference from said adjacent digits.

9. The method of claim 8, further comprising the steps of positioning said orthopedic device, with said selected digit and said adjacent digits disposed thereon on a surface; and taking an X-ray image of said selected digit.

* * * * *